(12) United States Patent
Choo et al.

(10) Patent No.: US 6,566,655 B1
(45) Date of Patent: May 20, 2003

(54) MULTI-BEAM SEM FOR SIDEWALL IMAGING

(75) Inventors: Bryan K. Choo, Mountain View, CA (US); Bhanwar Singh, Morgan Hill, CA (US); Sanjay K. Yedur, San Ramon, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 242 days.

(21) Appl. No.: 09/729,449

(22) Filed: Dec. 4, 2000

Related U.S. Application Data

(60) Provisional application No. 60/242,832, filed on Oct. 24, 2000.

(51) Int. Cl.[7] .......................... H01J 37/28; G01N 23/22
(52) U.S. Cl. .................. 250/310; 250/306; 250/396 R; 250/397; 250/492.2; 250/492.3
(58) Field of Search ................................. 250/310, 306, 250/396 R, 397, 492.2, 492.3

(56) References Cited

U.S. PATENT DOCUMENTS

| | | | | |
|---|---|---|---|---|
| 3,714,422 A | * | 1/1973 | Hosoki et al. | 250/49.5 A |
| 3,986,027 A | | 10/1976 | Holmes | 250/310 |
| 4,080,546 A | | 3/1978 | Steigerwald et al. | 313/348 |
| 4,916,315 A | | 4/1990 | Otaka | 250/310 |
| 5,029,250 A | | 7/1991 | Komatsu et al. | 250/310 |
| 5,192,867 A | | 3/1993 | Osakabe et al. | 250/311 |
| 5,612,535 A | | 3/1997 | Wang | 250/310 |
| 5,659,172 A | | 8/1997 | Wagner et al. | 250/307 |
| 5,767,521 A | | 6/1998 | Takeno et al. | 290/492.2 |
| 5,811,806 A | | 9/1998 | Honda et al. | 250/311 |
| 5,892,224 A | * | 4/1999 | Nakasuji | 250/310 |
| 5,900,937 A | | 5/1999 | Wang | 356/357 |
| 6,042,738 A | | 3/2000 | Casey, Jr. et al. | 216/66 |
| 6,124,140 A | * | 9/2000 | Do et al. | 438/10 |

OTHER PUBLICATIONS

Hassel, M. and Espeseth, R.; "In–Line SEM's for Defect Monitoring and Yield Enhancement", Semiconductor-Fabtech.com; http://www.semiconductorfabtech.com/features/tab/articles/03.231.html; viewed Jun. 23, 2000; pp. 1–8.

Irmer, B., et al., "Josephson Junctions Defined by a Nanoplough", Applied Physics Letters; Oct. 5, 1998; vol. 73, No. 14, pp. 2051–2053.

Jin, X. and Unertl, W.N.; "Submicrometer Modification of Polymer Surfaces with a Surface Force Microscope", Applied Physics Letters, Aug. 10, 1992, vol. 61, No. 6, pp. 657–659.

(List continued on next page.)

Primary Examiner—Bruce Anderson
Assistant Examiner—Nikita Wells
(74) Attorney, Agent, or Firm—Amin & Turocy, LLP

(57) ABSTRACT

The present invention provides a system and method that facilitates measuring and imaging topographical features of a substrate, including lines and trenches having reentrant profiles. One aspect of the invention provides an electron microscope that simultaneously scans a substrate with two or more electron beams that are directed against the substrate with substantially differing angles of incidence. Secondary electrons resulting from the interaction of the substrate with the beams are detected by one or more secondary electron detectors. Each secondary electron detector may simultaneously receive secondary electrons resulting from the interaction of the substrate with two or more electron beams. In another of its aspects, the invention provides methods of analysis that permit the interpretation of such data to analyze critical dimensions and form images of the substrate. Critical dimensions that may be determined include feature heights and reentrant profile shapes. The topographical information provided is more complete than that of conventional SEM imaging and is obtained more rapidly than would be possible using multiple scans of a single electron beam.

41 Claims, 9 Drawing Sheets

OTHER PUBLICATIONS

Majumdar, A., et al.; "Nanometer–Scale Lithography Using the Atomic Force Microscope", *Applied Physics Letters*, Nov. 9, 1992, vol. 61, No. 19, pp. 2293–2295.

Mamin, H.J. and Rugar, D.; "Thermomechanical Writing with an Atomic Force Microscope Tip", *Applied Physics Letters*, Aug. 24, 1992, vol. 61, No. 8, pp. 1003–1005.

Schumacher, H.W., et al.; "Nanomachining of Mesoscopic Electronic Devices Using an Atomic Force Microscope"; *Applied Physics Letters*, vol. 75, No. 8, pp. 1107–1109.

Sumomogi, T., et al.; "*Micromachining of Metal Surfaces by Scanning Probe Microscope*"; *Science Technology*; vol. 12, No. 3, pp. 1876–1880.

Wang, et al.; "*Nanometer–Structure Writing on Si(100) Surfaces Using a Non–Contact–Mode Atomic Forcer Microscope*"; *Applied Physics Letters*, vol. 65, No. 11, pp. 1415–1417.

\* cited by examiner

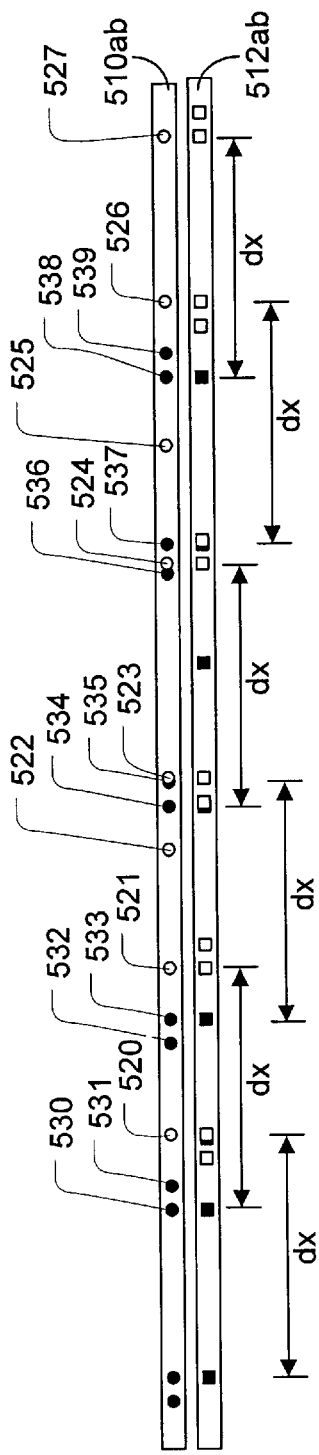
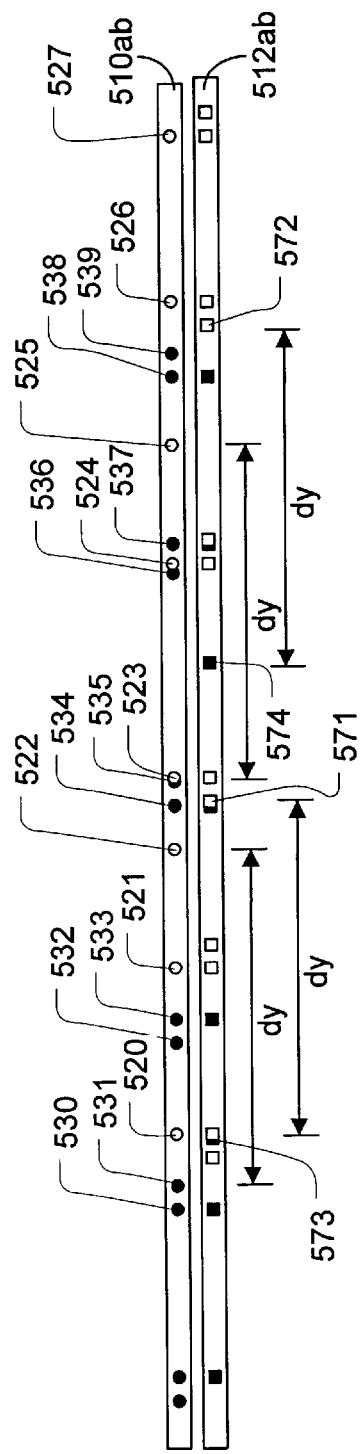
Fig. 5c
Fig. 5d

MULTI-BEAM SEM FOR SIDEWALL IMAGING

CROSS REFERENCE TO RELATED APPLICATIONS

This application claims the benefit of U.S. Provisional Patent Application Serial No. 60/242,832, filed Oct. 24, 2000, entitled MULTI-BEAM SEM FOR SIDEWALL IMAGING.

TECHNICAL FIELD

The present invention generally relates to semiconductor processing and, more particularly, to systems and methods for measuring and/or imaging features, such as lines and spaces, including those having reentrant profiles.

BACKGROUND OF THE INVENTION

In the semiconductor industry, there is a continuing trend toward higher device densities. To achieve these higher device densities there have been, and continue to be, efforts toward scaling down the device dimensions on semiconductor wafers. In order to accomplish higher device densities, smaller and smaller features sizes are required. These may include the width and spacing of interconnecting lines, spacing and diameter of contact holes, and surface geometry of corners and edges of various features.

High resolution lithographic processes are used to achieve small features. In general, lithography refers to processes for pattern transfer between various media. In lithography for integrated circuit fabrication, a silicon slice, the wafer, is coated uniformly with a radiation-sensitive film, the resist. The film is selectively exposed with radiation (such as optical light, x-rays, or an electron beam) through an intervening master template, the mask, forming a particular pattern. Exposed areas of the coating become either more or less soluble than the unexposed areas (depending on the type of coating) in a particular solvent developer. The more soluble areas are removed with the developer in a developing step. The less soluble areas remain on the silicon wafer forming a patterned coating. The pattern corresponds to the image of the mask or its negative. The patterned resist is used in further processing of the silicon wafer.

At various stages in forming the patterned resist coating and processing the silicon wafer, it is desirable to measure critical dimensions resulting from the lithographic process. Critical dimensions include the size of features in the wafer or patterned resist such as line widths, line spacing, and contact dimensions. Due to the extremely fine patterns involved, Scanning Electron Microscopy (SEM) is often employed to analyze critical dimensions.

In SEM, an electron beam is scanned across the sample. The beam interacts with the sample to produce measurable responses that vary with position over the course of a scan. Measurable responses include backscattering of electrons and production of secondary electrons, auger electrons, X-rays and cathodoluminescence. Secondary electrons are the most useful of the measurable responses in accessing surface topography and are the responses most often measured in critical dimension analysis. A secondary electron detector is used to measure the variation in secondary electron intensity over the course of a scan. An image formed of secondary electron intensity measurements is comparable to a black and white picture of the surface taken from the perspective of the electron beam with illumination coming from the position of the secondary electron detector.

While such images are useful is critical dimension analysis, they have some important limitations. For example, in certain fabrication processes, resist and/or etched features have cross-sectional profiles that are reentrant. By "reentrant profile," it is meant that feature sidewalls taper inwardly towards the base of the feature. For an elongated feature, such as a line or space, a reentrant profile may result in an elongated trench (e.g., having a trapezoidal cross section) positioned along the juncture of the feature and the substrate surface adjacent the feature. While reentrant profiles may be desirable in certain circumstances, the reentrant features may cause a shadowing effect during subsequent deposition. As a result of the shadowing effect by the upper portion of the feature, an elongated void may be formed during the deposition at the base of the reentrant feature where it contacts the substrate. The void, if undetected, may have serious consequences for subsequent processing steps and may result in defects that compromise the operation of the resulting semiconductor device. Conventional SEM systems for measuring critical dimensions of wafers often fail to detect reentrant profiles of lines and/or spaces.

It is desirable to have systems and methods that facilitate measuring and/or imaging a feature, such as a line and/or trench, having a reentrant profile.

SUMMARY OF THE INVENTION

The present invention provides a system and method that facilitates measuring and imaging topographical features of a substrate, including lines and trenches having reentrant profiles. One aspect of the invention provides an electron microscope that simultaneously scans a substrate with two or more electron beams that are directed against the substrate with substantially differing angles of incidence. Secondary electrons resulting from the interaction of the substrate with the beams are detected by one or more secondary electron detectors. Each secondary electron detector may simultaneously receive secondary electrons resulting from the interaction of the substrate with two or more electron beams. In another of its aspects, the invention provides methods of analysis that permit the interpretation of such data to analyze critical dimensions and form images of the substrate. Critical dimensions that may be determined include feature heights and reentrant profile shapes. The topographical information provided is more complete than that of conventional SEM imaging and is obtained more rapidly than would be possible using multiple scans of a single electron beam.

One aspect of the invention provides a scanning electron microscope including an electron beam source, electromagnetic elements configured to simultaneously direct with substantially differing angles of incidence a first and a second electron beam against a substrate, and a first secondary electron detector configured to detect at least secondary electrons resulting from an interaction of the substrate with the first electron beam Another aspect of the invention provides a system for measuring a characteristic of a reentrant topographical feature of a substrate including means for simultaneously directing two or more electron beams at the substrate surface wherein two of the beams are directed at angles differing by at least about 10 degrees, and means for detecting secondary electrons produced by the interaction of the substrate with the electron beams.

A further aspect of the invention provides a method for assessing a characteristic of a feature of a substrate surface, the method including scanning the substrate simultaneously employing first and second electron beams directed against the substrate, the first and second electron beams having angles of incidence that differ by at least about 10 degrees, detecting secondary electrons produced by interaction of the first and second electron beams with the substrate to generate secondary electron data, and analyzing the secondary electron data to assess the characteristic of the feature of the substrate surface.

A further aspect of the invention provides a scanning electron microscope system including an electron beam source, electromagnetic elements for simultaneously directing first and second electron beams derived from the electron beam source against a substrate, a first secondary electron detector for simultaneously detecting secondary electrons resulting from the interaction of the substrate with the first electron beam and secondary electrons resulting from the interaction of the substrate with the second electron beam and for sending data relating to the secondary electrons detected, and a processor for receiving and analyzing the data from the secondary electron detector.

A further aspect of the invention provides a system for measuring a characteristic of a reentrant topographical feature of a substrate, including means for simultaneously directing two or more electron beams at the substrate, the beams having angles differing by at least about 10 degrees, means for detecting secondary electrons resulting from the interaction of the substrate with the electron beams and producing secondary electron data, and means for analyzing secondary electron data, wherein the secondary electrons resulting from the interaction of the substrate with two or more of the electron beams are detected together.

A further aspect of the invention provides a method for assessing a characteristic of a feature of a substrate surface, the method including scanning the substrate simultaneously employing first and second electron beams directed against the substrate, detecting secondary electrons resulting from an interaction of the first electron beam with the substrate together with secondary electrons resulting from an interaction of the second electron beam with the substrate to generate secondary electron data, and analyzing the secondary electron data to assess the characteristic of the feature of the substrate surface.

The invention extends to features hereinafter fully described and features particularly pointed out in the claims. The following detailed description and the annexed drawings set forth in detail certain illustrative examples of the invention. These examples are indicative of but a few of the various ways in which the principles of the invention may be employed. Other ways in which the principles of the invention may be employed and other objects, advantages and novel features of the invention will be apparent from the detailed description of the invention when consider in conjunction with the drawings.

BRIEF DESCRIPTION OF THE DRAWINGS

FIG. 4b is an illustration of a method of constructing an image of a feature employing scan data of the type illustrated in FIGS. 3 and 4a.

FIG. 5c is an illustration of showing some relationships among the relative positions of the transition points in secondary electron data illustrated in FIGS. 5a and 5b.

FIG. 5d is an illustration of showing some other relationships among the relative positions of the transition points in secondary electron data illustrated in FIGS. 5a and 5b.

DETAILED DESCRIPTION OF THE INVENTION

Figure 1A:
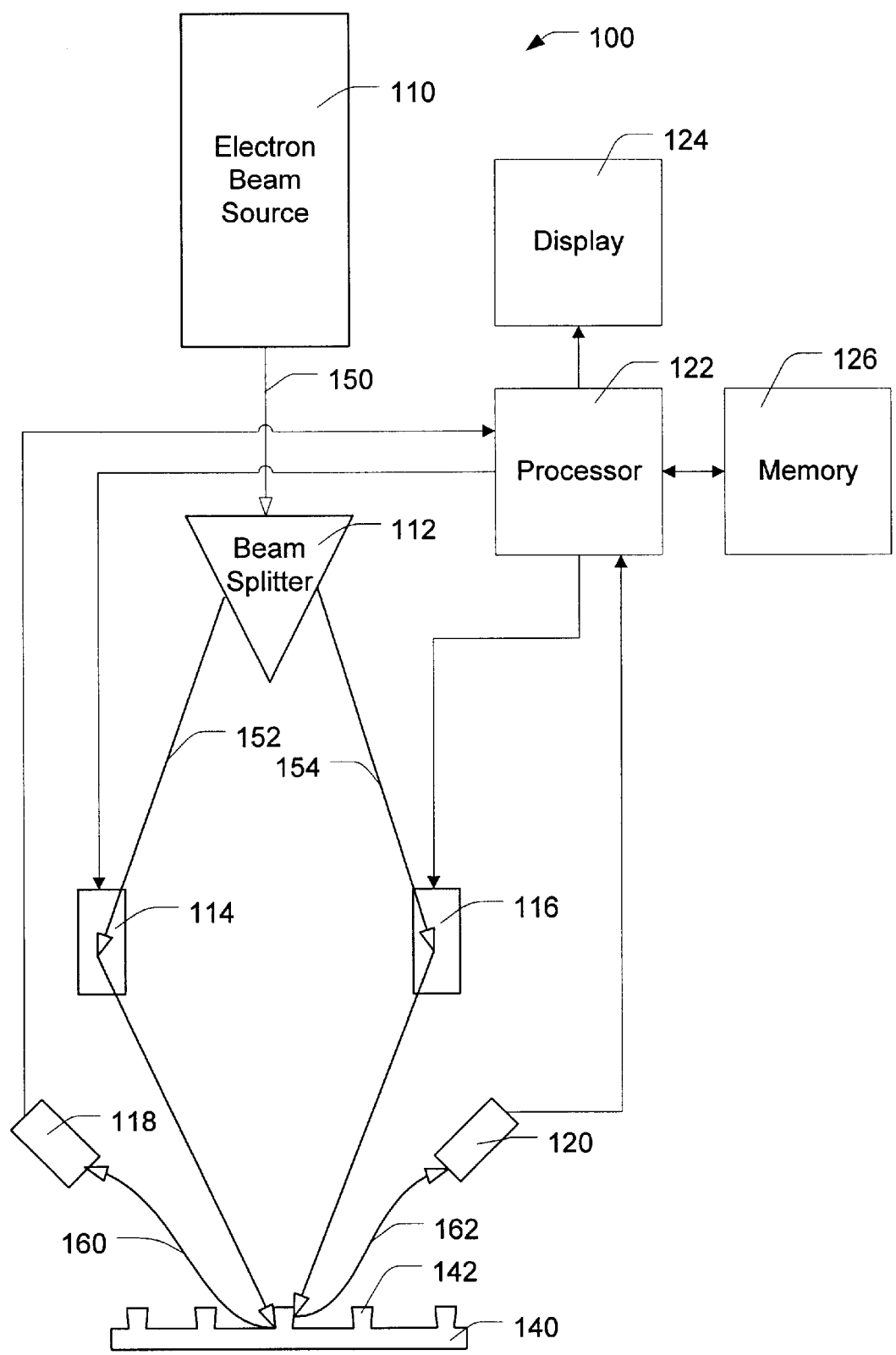
FIG. 1a is a schematic of an SEM system according to one aspect of the present invention.

The present invention will now be described with reference to the drawings, wherein like reference numerals are used to refer to like elements throughout.

The present invention provides a system and method for obtaining information regarding the topography of a substrate surface. FIG. 1 is a schematic illustration of a SEM system 100 according to one aspect of the present invention. SEM system 100 includes electron beam source 110, electron beam splitter 112, electromagnetic elements 114 and 116, secondary electron detectors 118 and 120, processor 122, memory 126, and display 124. Electron beam 150 from electron beam source 110 is divided into electron beams 152 and 154 by beam splitter 112. Electromagnetic elements 114 and 116 redirect and focus electron beams 152 and 154 onto substrate 140. Electron beams 152 and 154 strike substrate 140 with substantially differing angles of incidence, whereby characteristics of reentrant features 142 of substrate 140 may be assessed. Secondary electrons released by substrate 140 are detected by secondary electron detectors 118 and 120. Data from secondary electron detectors 118 and 120 is gathered by processor 122 and stored in memory 126. When sufficient data has been gather, processor 122 analyzes the data and displays results on display 124. The results may include images, critical dimension measurements, and/or profiles of substrate features, including reentrant profiles.

Electron beam source 110, which provides electron beam 150, may be any source suitable for use in SEM. Electron beam source 110 may include multiple electron beam sources. The electron beam particles may be accelerated, for example, to an energy in the range from about 500 eV to about 40 Kev. Various electromagnetic elements may be used to guide and focus electron beam 150 on electron beam splitter 112.

Electron beam splitter 112 divides electron beam 150 into two or more beams. Where multiple electron beam sources are used, electron beam splitter 112 may be omitted. Electron beam splitter 112 may be any device suitable for dividing one electron beam into two or more electron beams. For example, electron beam splitter 112 may be a plate with multiple apertures, a Mollenstedt biprism with two electrodes and a central wire, or a spin-split electron beam splitter. Multiple beam splitters may be used to provide more than two electron beams for scanning substrate 140. Beam splitter 112 is advantageously of a type, such as a spin-split electron beam splitter, that gives electron beams 152 and 154 diverging angles, whereby the beams are more easily directed to electromagnetic elements 114 and 116.

Electromagnetic elements 114 and 116 may be any combination of electromagnetic elements suitable for redirecting and focusing electron beams 152 and 154 onto substrate 140. Electromagnetic elements 114 and 116 may direct electron beams 152 and 154 onto substrate 140 at locations in proximity to one another, which has advantages described below. However, in one aspect of the invention, electromagnetic elements 114 and 116 direct electron beams 152 and 154 onto substrate 140 at locations that are at least about 1 micron apart to facilitate separate detection of secondary electrons resulting from the interaction of substrate 140 with electron beam 152 and secondary electrons resulting from the interaction of substrate 140 with electron beam 154. In another aspect of the invention, the locations are at least about 10 microns apart. In a further aspect of the invention, the locations are at least about 100 microns apart.

Electromagnetic elements 114 and 116 direct electron beams 152 and 154 onto substrate 140 at substantially differing angles of incidence. Substantially differing angles of incidence are angles that differ sufficiently to permit imaging of both sides of a raised line or trench with a reentrant profile. The greater the differences in angle, and the greater the angle of each beam's inclination with respect to an imaginary plane perpendicular to the surface of substrate 140, the deeper the extent of undercutting that may be imaged. Generally the angles of incidence of the beams differ by at least about 10 degrees, each beam being inclined at least about 5 degrees from an imaginary plane perpendicular to the surface of substrate 140. In one aspect of the invention, the difference in angle between the two beams is from about 20 degrees to about 160 degrees. In another aspect of the invention, the difference in angle is from at least about 30 degrees to about 90 degrees. In each of the forgoing cases, the beams may form angles that are approximately symmetric about an imaginary line or plane perpendicular to substrate 140, although such symmetry is not required.

Electromagnetic elements 114 and 116 may also provide for varying the angle of electron beams 152 and 154 to effectuate a scan of substrate 140. The variation in angle by which electron beams 152 and 154 scan substrate 140 may be small in comparison to the angles the beams make with each other or with an imaginary line or plane perpendicular to the surface of substrate 140 because the substrate is generally small in comparison to the distances of electromagnetic elements 114 and 116 from substrate 140. FIG. 1a is a schematic illustration and does not show these proportions.

While electromagnetic elements 114 and 116 may vary the directions of electron beams 152 and 154 in order to scan across substrate 140, alternatively the directions of electron beams 152 and 154 may remain approximately fixed while substrate 140 moves to effectuate a scan. For example, substrate 140 may be placed on a moving sample stage. The required precision of movement in the vacuum environment of a scanning electron microscope chamber may be achieved using piezoelectric motors, for example.

Over the course of a scan, secondary electrons resulting from interactions of substrate 140 with electron beams 152 and 154 are detected by secondary electron detectors 118 and 120. Secondary electron detectors 118 and 120 can be of any of the types used in SEM to measure number or flux (numbers per unit time) of secondary electrons. Secondary electron detectors 118 and 120 provide processor 132 with a signal that includes secondary electron data such as number or flux of secondary electrons detected.

Secondary electron detector 118 is generally positioned such that an imaginary line from secondary electron detector 118 to where electron beam 152 strikes substrate 140 is inclined at least as far from an imaginary plane perpendicular to substrate 140 as is electron beam 152. In one aspect of the invention, secondary electron detector 118 is inclined at least about 2 degrees further from the imaginary plane than electron beam 152. In a further aspect of the invention, secondary electron detector 118 is inclined at least about 5 degrees further from the imaginary plane than electron beam 152. Secondary electron detector 120 is similarly inclined from the imaginary plane, but to the same side as electron beam 154. These secondary electron detector positions permit detection of secondary electrons emitted when an electron beam strikes the side of a feature having a reentrant profile.

Various elements may be used to regulate the flow of secondary electrons from substrate 140 to secondary electron detectors 118 and 120. Electromagnetic elements, such as charged particle lenses, may be used to guide secondary electrons to the detectors, thereby increasing the strength of the secondary electron signal. Apertures, plates, and electromagnetic elements of different types, may be used to limit which secondary electrons reach each detector, increasing the extent to which points of origin of detected secondary electrons are determined.

While these various elements may be configured to allow individual secondary electron detectors to be associated with individual electron beams, according to one aspect of the invention, an individual secondary electron detector receives secondary electrons produced by the interaction of substrate 140 with two or more electron beams. In another aspect of the invention, each secondary electron detector essentially detects only secondary electrons produced in response to one electron beam.

Figure 1B:
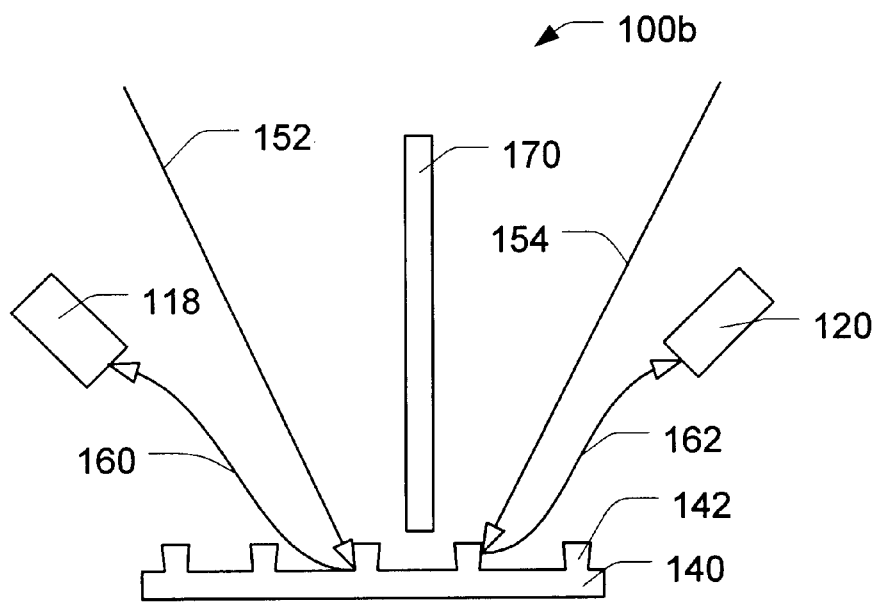
FIG. 1b is a schematic of a portion of an SEM system according to another aspect of the present invention.

FIG. 1b illustrates a portion of a system 100b in which each of two secondary electron detectors essentially detects only secondary electrons resulting from the interaction of substrate 140 with one of two electron beams. System 100b includes plate 170, which provides a barrier against secondary electrons. In system 100b, the probability of secondary electrons resulting from the interaction of substrate 140 with electron beam 154 reaching secondary electron detector 118 is very small, as is the probability of secondary electrons resulting from the interaction of substrate 140 with electron beam 152 reaching secondary electron detector 120.

Figure 1C:
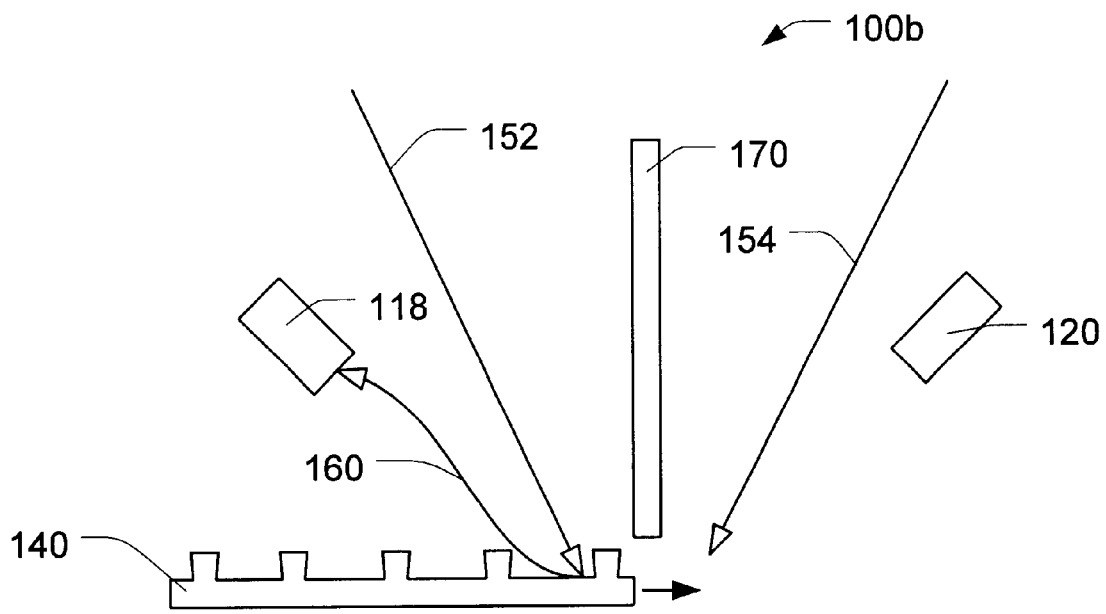
FIG. 1c is a schematic of the portion of an SEM system illustrated in FIG. 1b, but with the substrate translated relative to the plate 170.
Figure 1D:
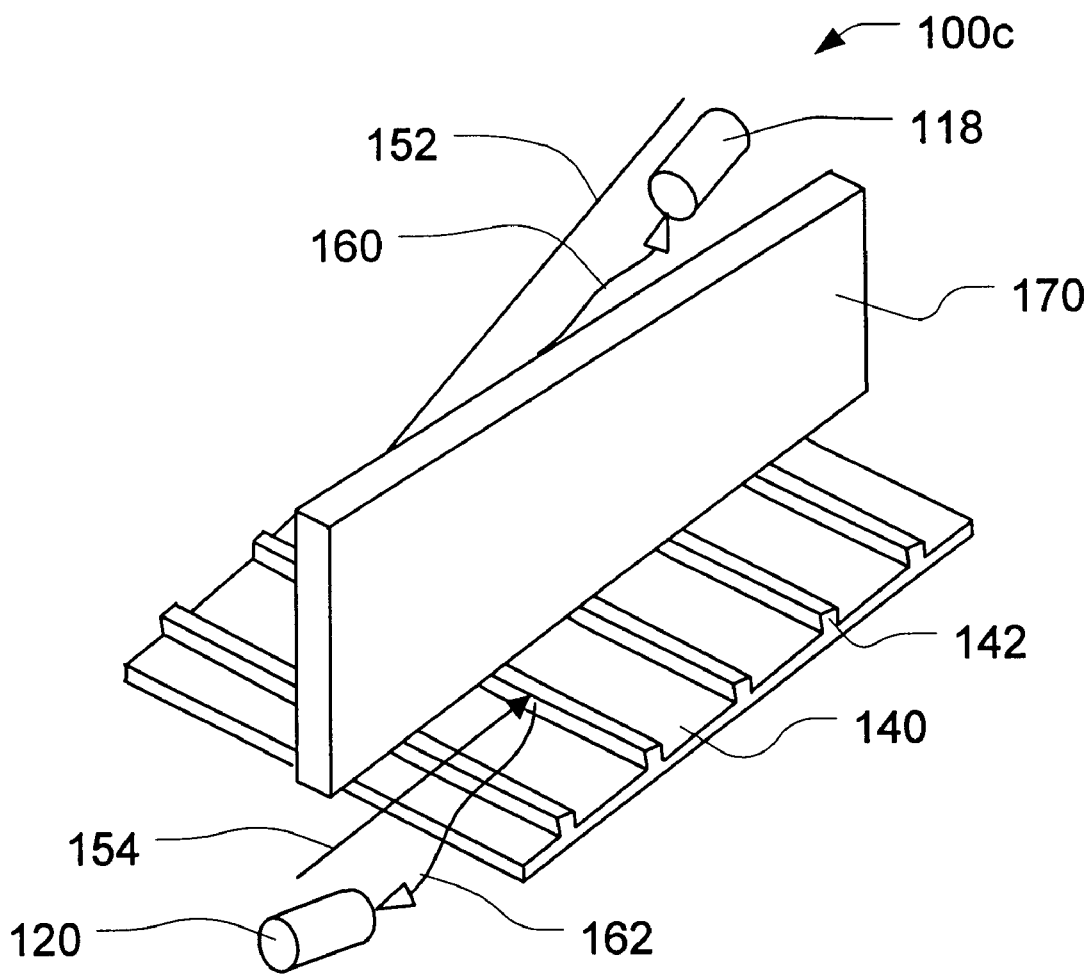
FIG. 1d is a schematic of a portion of an SEM system according to a further aspect of the present invention.

FIG. 1d illustrates another system 100d in which the secondary electrons are segregated. Like system 100b, system 100d uses a plate 170 as a barrier against secondary electrons. In system 100d, the orientations of electron beams 152 and 154 and secondary electron detectors 118 and 120 further reduce the probability of a single secondary electron detector receiving signals in response to two or more beams.

Although the illustrations show systems with two secondary electron detectors, there can be any number. In some cases, one secondary electron detector is sufficient, although in most cases there are at least as many secondary electron detectors as there are electron beams. Greater numbers of detectors increase the amount of information that may be obtained from a given scan. For example, in a system using two electron beams, using four secondary electron detectors improves accuracy and reliability of critical dimension measurements in comparison to using two secondary electron detectors without increasing scan time.

The signals provided by secondary electron detectors 118 and 120, which may be analog or digital, are received by processor 132, optionally after signal processing such as filtration and/or amplification. Processor 132 may store the signal data in memory 126. When sufficient data is available, processor 132 analyzes the data to calculate critical dimensions of substrate 140, for example. Optionally, processor 132 may construct an image of substrate 140 from the data and display the image on display 124.

Processor 132 may control the scanning of substrate 140. The control may be implemented through directing the motion of a sample stage, directing beams 152 and 154 through electromagnetic elements 114 and 116, or a combination of the foregoing. Memory 126 may be employed to store software instructions for processor 132.

Generally, substrate 140 is of any type and may be a semiconductor substrate in particular. Semiconductor substrates include a semiconducting material, such as silicon. In addition to a semiconducting material, the substrate may include various elements and/or layers, including metal layers, barrier layers, dielectric layers, device structures, active elements and passive elements including silicon gates, word lines, source regions, drain regions, bit lines, bases emitters, collectors, conductive lines, conductive plugs, etc. The substrate may have a conductive coating applied to facilitate SEM. Substrate 140 has a surface with features 142. The surface of substrate 140 is generally flat in its gross aspect, while having features 142 on a microscopic or sub-microscopic scale.

Figure 2:
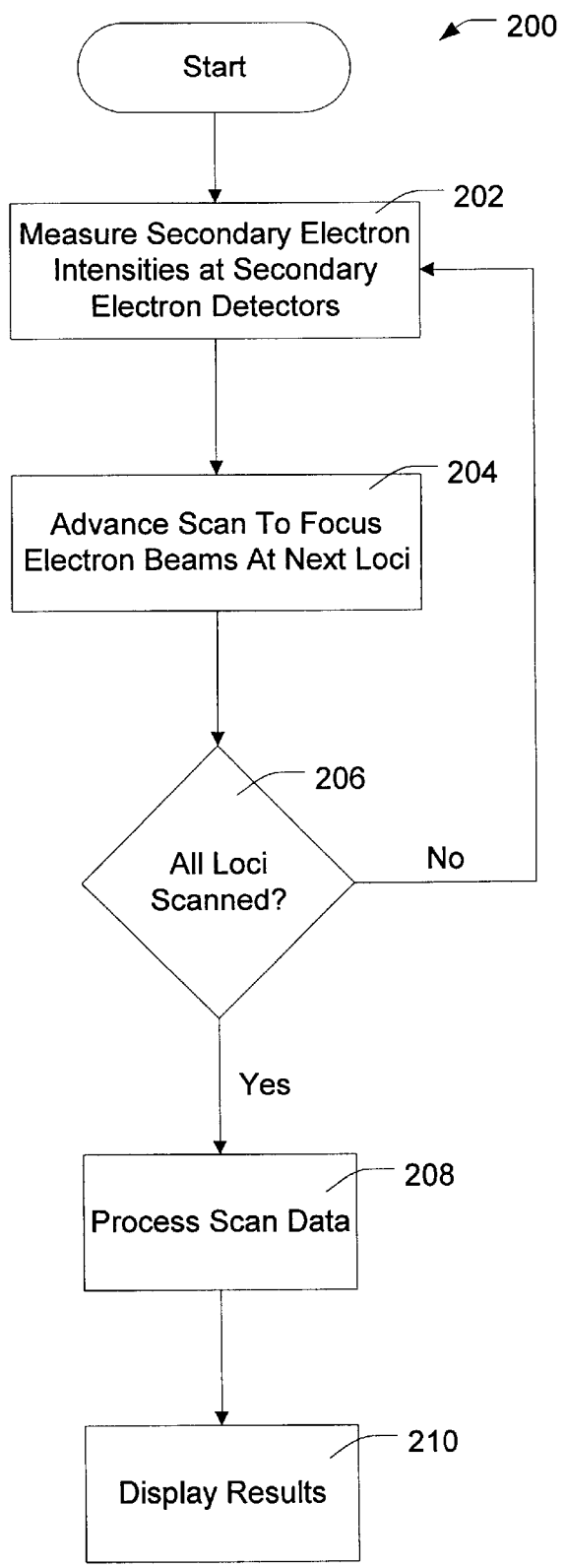
FIG. 2 is a block flow diagram of a process for obtaining topographical information according to one aspect of the present invention.

The systems of the invention scan substrate 140 with at least two electron beams having between them at least two different angles of incidence with respect to substrate 140. FIG. 2a is a flow diagram of a scanning protocol 200 in accordance with one aspect of the present invention. In step 202, secondary electron intensities are measured by secondary electron detectors. The secondary electron intensities correspond to the rates at which secondary electrons reach the detectors while the electron beams are focused on particular loci on the surface of substrate 140. In step 204, the electron beams scan to new locations. Where a scan is continuous, steps 202 and 204 are simultaneous. In step 206, there is a check whether the scan is complete. The scan is complete when every loci of interest has been scanned with electron beams incident from at least two different directions. When the scan is complete, the data gathered from the secondary electron detectors is analyzed in step 208 to assess a characteristic of the substrate surface topography. The characteristic may be, for example, a critical dimension such as a feature's upper width, lower width, or height, the feature's profile, or the feature's image. Optionally, the data analysis may begin before the scan is complete.

There are a variety of methods by which every loci of interest may be scanned. Scanning may involve moving substrate 140 on a sample stage. In systems 100b and 100d, which include plate 170, the sample stage causes each loci of interest on the surface of substrate 140 to travel from one side of plate 170 to the other over the course of the scan, as illustrated in FIG. 1c. Alternatively, the electron beams may be scanned over the stationary substrate. For systems 100b and 100d, one option is to move plate 170 synchronously with the electron beams sweeping across substrate 140. Another option is to scan the portion of substrate 140 on one side of plate 170 with one beam while the portion of substrate 140 on the other side of plate 170 is scanned by the other beam. Substrate 140 is then rotated so that the portions of substrate 140 switch sides of the plate. Each beam then scans the portion of substrate 140 previously scanned by the other beam. The method of scanning, particularly the question of whether the substrate is to be rotated, affects the selection of the secondary electron detector positions and the electron beam orientations.

Figure 3:
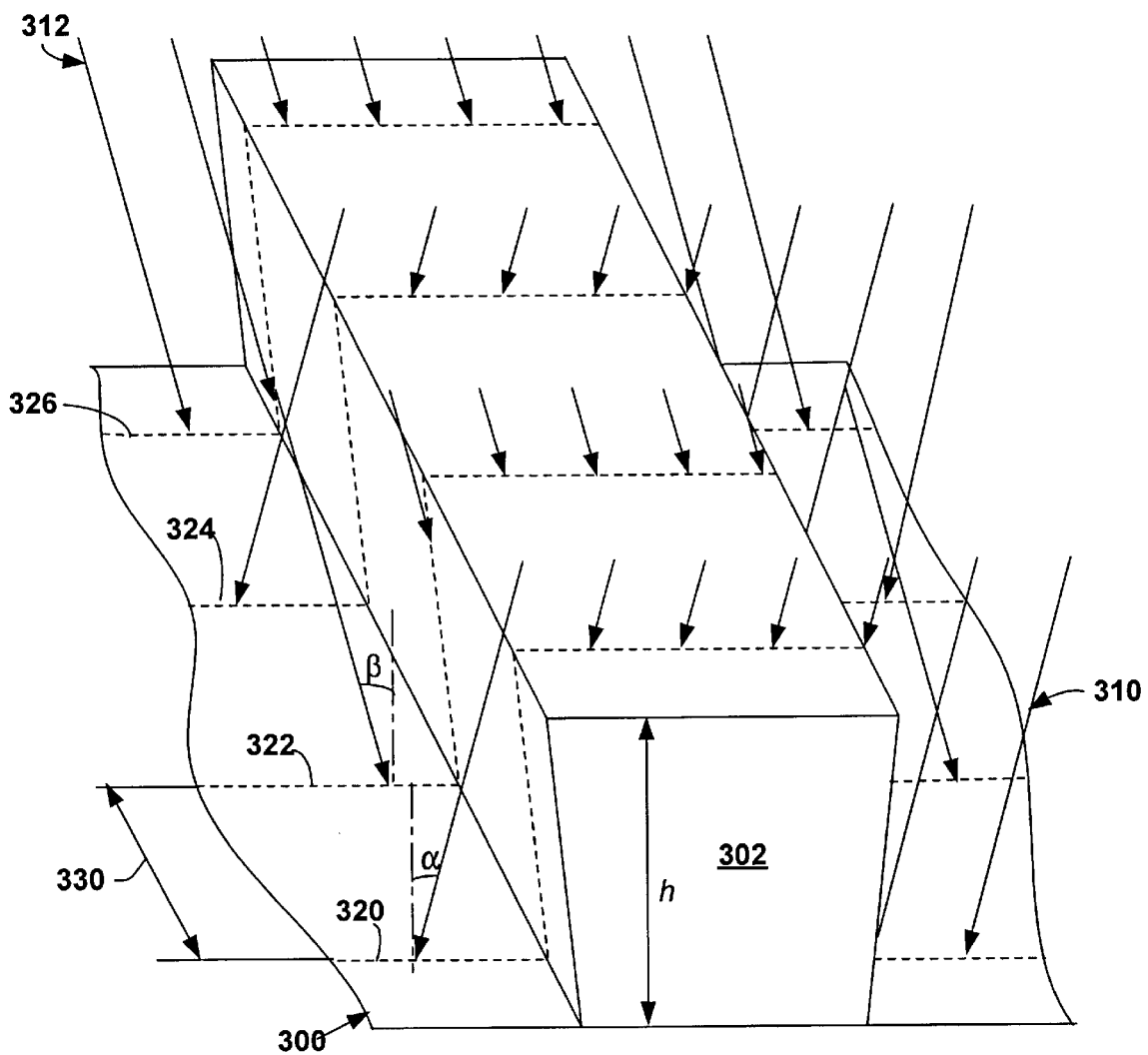
FIG. 3 is an oblique view illustration of a substrate being scanned according to one aspect of the present invention.

In scanning every loci of interest, the beams may travel identical paths, or path that are merely close to one another. FIG. 3a illustrates, with an isometric view, a scanning pattern over substrate 300, which includes an elongated feature, line 302. Line 302 is scanned by electron beams 310 and 312, which have angles of incidence $\alpha$ and $\beta$ respectively, with respect to substrate 300. Scan paths for the electron beams are marked by broken lines 320, 322, 324, and 326. Beam 310 scans along paths 320 and 324. Beam 312 scans along paths 322 and 326. Scans along paths 320 and 322 are considered as scanning one loci of line 302, while scans along paths 324 and 326 are considered as scanning another loci of line 302. The distance between scans of beams 310 and 312 over one loci of line 312, illustrated by the distance 330 between scans 320 and 322, is sufficiently small that it may be reasonably assumed the profile of line 302 does not change significantly between the one scan path and the other.

Secondary electron data may be analyzed in a variety of ways, depending on the configuration of the SEM system, what is presently known about the substrate, and what is desired to be known about a substrate. For example, an SEM system having two secondary electron detectors, each associated with one of two electron beams, may be used to determine the extent of undercutting of feature 302 of substrate 300, where the height of feature 302, h, is known. The feature 302 may have been formed, for example, by etching through a coating of known thickness, h, which was formed on the surface of substrate 300.

Figure 4A:
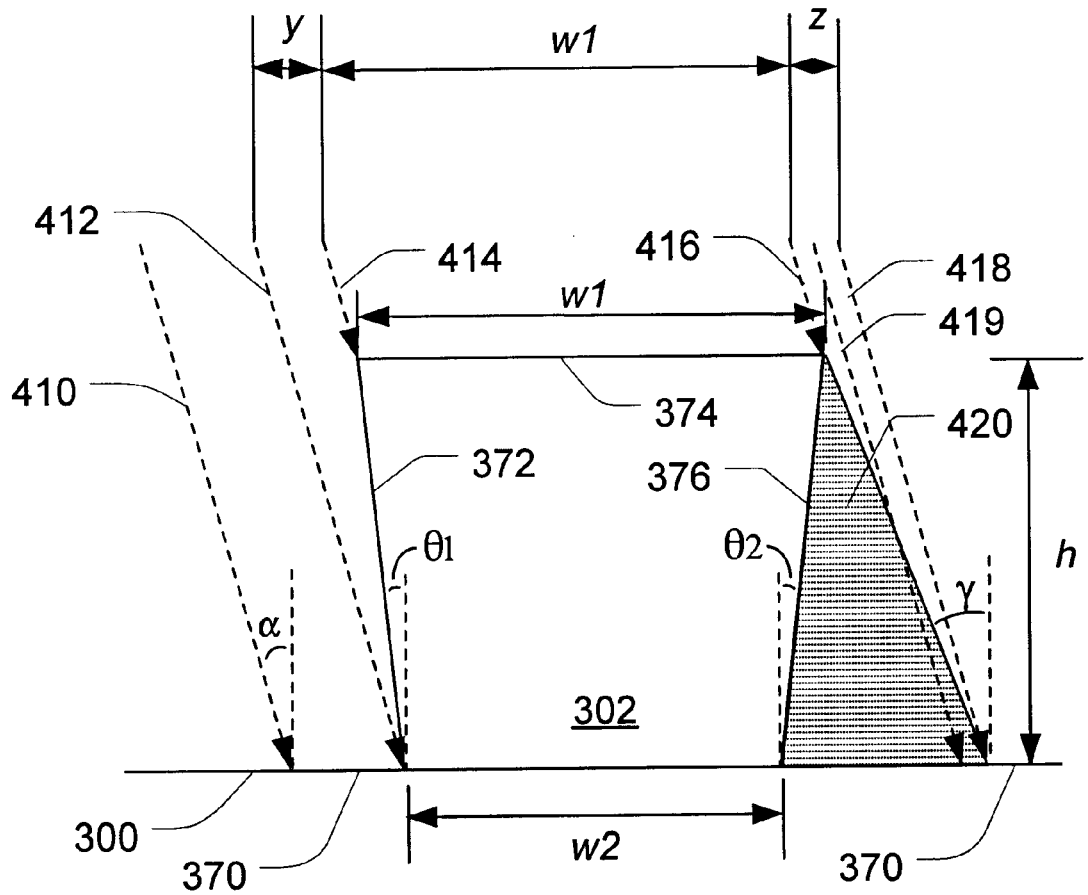
FIG. 4a is a cross-sectional illustration of a wafer feature showing the locations of critical beam positions that may be used to calculate critical dimensions of the feature.

In an example method of analyzing the data, the location 412, illustrated in FIG. 4a, at which an electron beam strikes the base of feature 302 is determined by examining the secondary electron data. When an electron beam and secondary electron detector are at suitable angles with respect to the substrate 300, the secondary electron intensity undergoes an abrupt transition as the beam passes location 412. Prior to reaching location 412, at beam position 410 for example, the secondary electron intensity is at a first level, which is determined by the nature of surface 370, the angle $\alpha$ the electron beam makes with an imaginary line perpendicular to the surface of substrate 300, and the position of the secondary electron detector. The angle of the electron beam, $\alpha$, is greater than the angle of undercutting, $\theta 1$, of feature 302. After passing location 412, the electron beam strikes surface 372 at the side of feature 302, resulting in a second secondary electron intensity level. The secondary electron detector, which in not shown in FIG. 4a, is positioned to receive secondary electrons released when the electron beam strikes surface 372. An imaginary line from substrate 300 to the detector makes an angle $\gamma$ with an imaginary line perpendicular to the surface of substrate 300. The angle $\gamma$ is greater than the undercut angle $\theta 1$.

The beam scans up surface 372 until it reaches location 414, where a second abrupt transition in the secondary electron intensity is observed, this time as the electron beam rounds the corner of feature 302 and begins to strike surface 374. From the beam angle α, the feature height h, and the relative displacement of the substrate and beam, y, between the first and second abrupt transitions, the angle of undercut θ1 may be calculated using the formula:

$$\theta 1 = \arctan\left(\tan(\alpha) - \frac{y}{h}\right)$$

Additional information may also be gathered from the scan. A third abrupt transition is observed at beam position 416, particularly if the secondary electron detector angle γ is greater than the beam angle α. Under such circumstances, the electron beam just beyond beam position 416, at beam position 419 for example, strikes the surface 370 within region 420, which is shaded from the secondary electron detector by the feature 302. Few, if any, secondary electrons generated within this region reach the secondary electron detector. The relative displacement of substrate and beam between the second and third transitions gives the width, w1, of feature 312 at its upper surface.

The height of feature 312 may be determined where it is not known in advance. A fourth transition in secondary electron intensity is observed when the electron beam reaches position 418. At beam position 418, the electron beam passes from region 420 to where it strikes the surface of substrate 300 at a position that is not shaded from the secondary electron detector. The relative displacement, z, of substrate and electron beam between the third and fourth transitions may be used to calculate the feature height:

$$h = \frac{z}{\tan(\gamma) - \tan(\alpha)}$$

To complete the measurement of feature 302, a second scan of feature 302 is analyzed. This second scan employs an electron beam and a secondary electron detector positioned to scan the right side of feature 302 and permits calculation of the right side angle of undercut, θ2. Once both angles of undercut, the feature height, and the width of feature 302 at its upper surface are determined, the width of feature 302 at its base, w2, may be calculated.

Figure 4B:
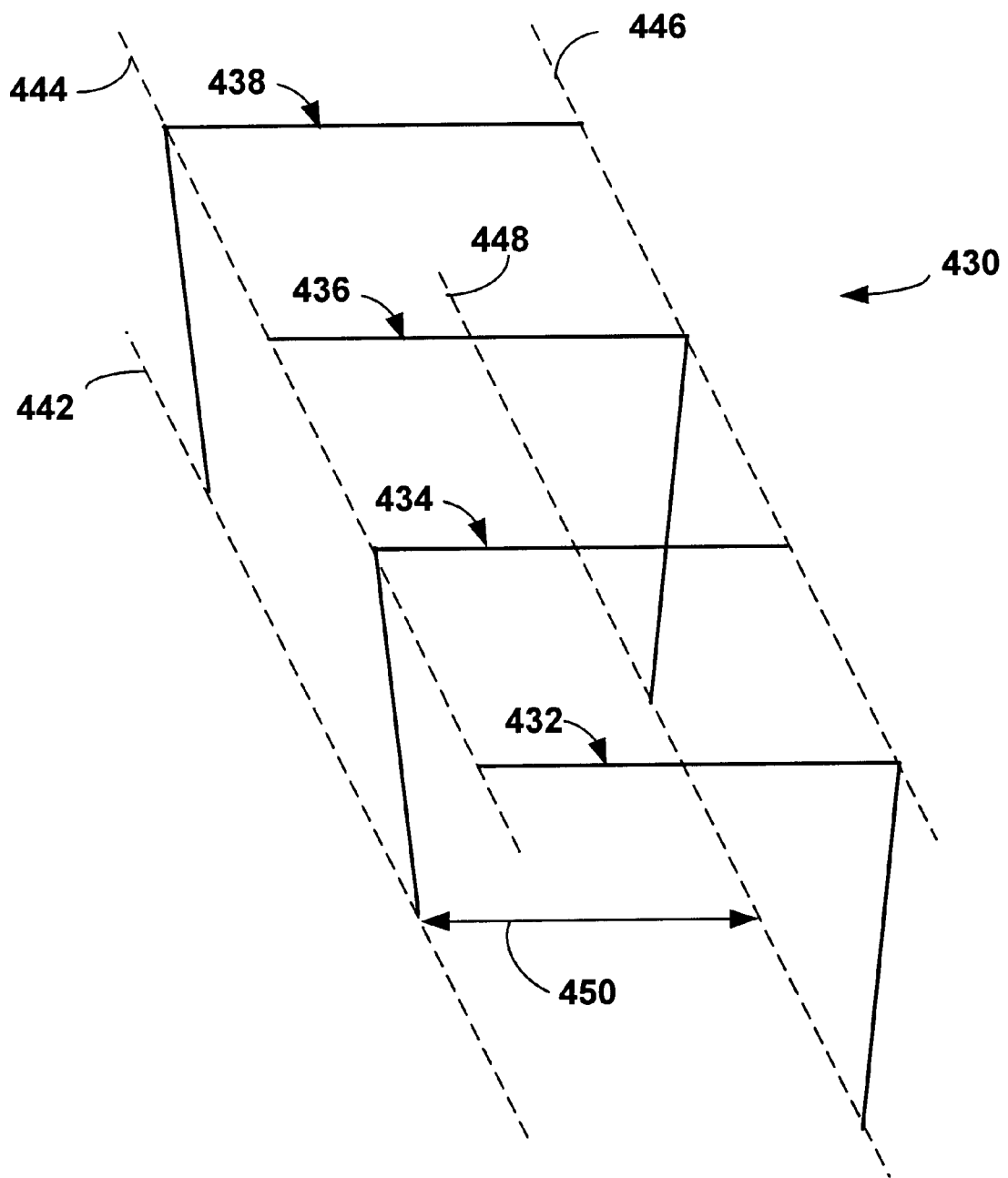

The first and second scans may occur over substantially the same cross-sectional path of the feature or over paths spaced apart a small distance along the feature's length. FIG. 4b illustrates a methodology that may be employed to determine critical dimensions of a feature using scans that are spaced apart by a small distance. In this example, an image 430 of a feature profile is constructed by aggregating image portions 432, 434, 436, and 438 corresponding to data obtained during different scans of feature 302. The image portions 432 and 436 correspond to critical dimension data obtained from scans with an electron beam oriented at a first angle relative to the substrate 300, as illustrated in FIG. 4a, and image portions 434 and 438 correspond to critical dimension data obtained from scans with an electron beam oriented at a second angle relative to the substrate 300.

The ends and vertex of each image portion 432, 434, 436, and 438 may be used to define feature boundaries of the image 430. Specifically, feature boundaries may be defined with virtual connecting lines 442, 444, 446, and 448 drawn through the corresponding vertexes and endpoints of each image portion. While, for purposes of simplicity of illustration, the virtual connecting lines 442, 444, 446, and 448 are shown to be linear, other line shapes may be employed commensurate with the secondary electron data and whatever else is known of the feature profile.

Critical dimensions of feature 302 may be calculated from virtual connecting lines 442–448 at any point along the feature image 430. By way of example, a critical dimension measurement at the base of feature 302 (at the juncture between feature 302 and the substrate) may be obtained based on the distance of between virtual connecting lines 442, 444, 446, and 448. For example, an imaginary line 450 may be drawn to connect the virtual lines 442 and 448 (corresponding to lower feature boundaries). The length of line 450 corresponds to a critical dimension of a lower portion of feature 302.

Similar techniques may be employed to determine critical dimensions from data obtained where individual secondary electron detectors receive secondary electrons resulting from the interaction of the substrate with multiple electron beams. Transitions observed by secondary electron detectors in such cases are caused by the interaction of the substrate with either one or another electron beam. Transitions caused by the interaction of the substrate with one beam are distinguished from transitions caused by the interaction of the substrate with another other beam by such factors as the nature of the variations in secondary electron intensity around the transition points (increasing or decreasing, size of variation, smoothness of variation, etc.), patterns of transition points, and comparisons between data from multiple secondary electron detectors.

Figure 5A:
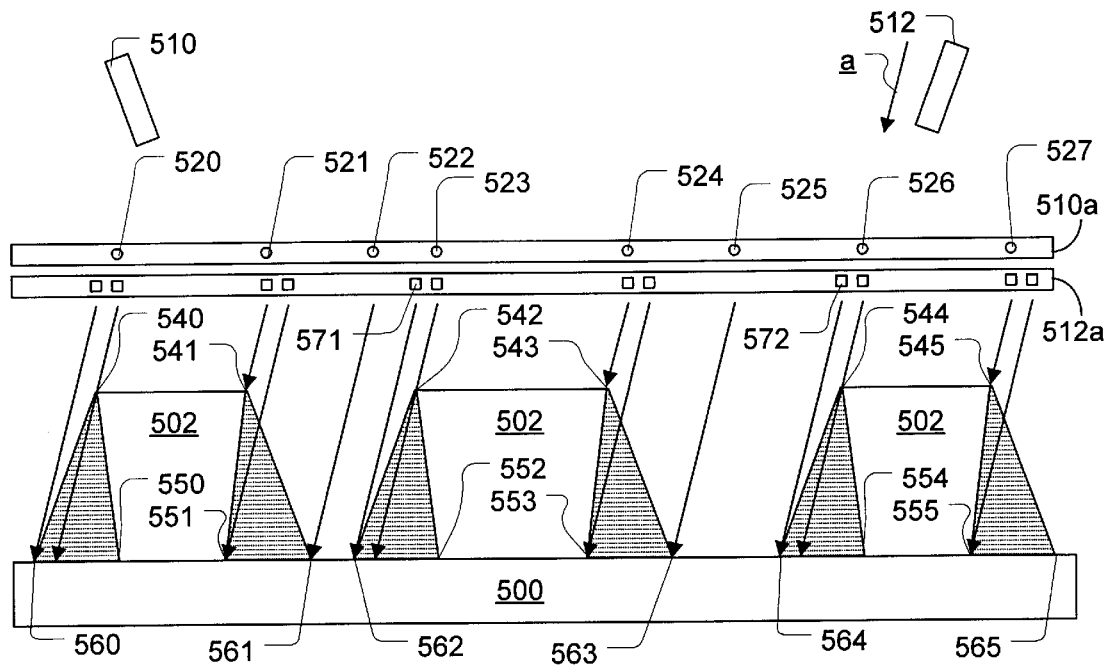
FIG. 5a is a cross-sectional illustration of a substrate showing critical positions of one of the beams employed in a scan and the transition points in secondary electron data resulting from the interaction of that beam with the substrate.
Figure 5B:
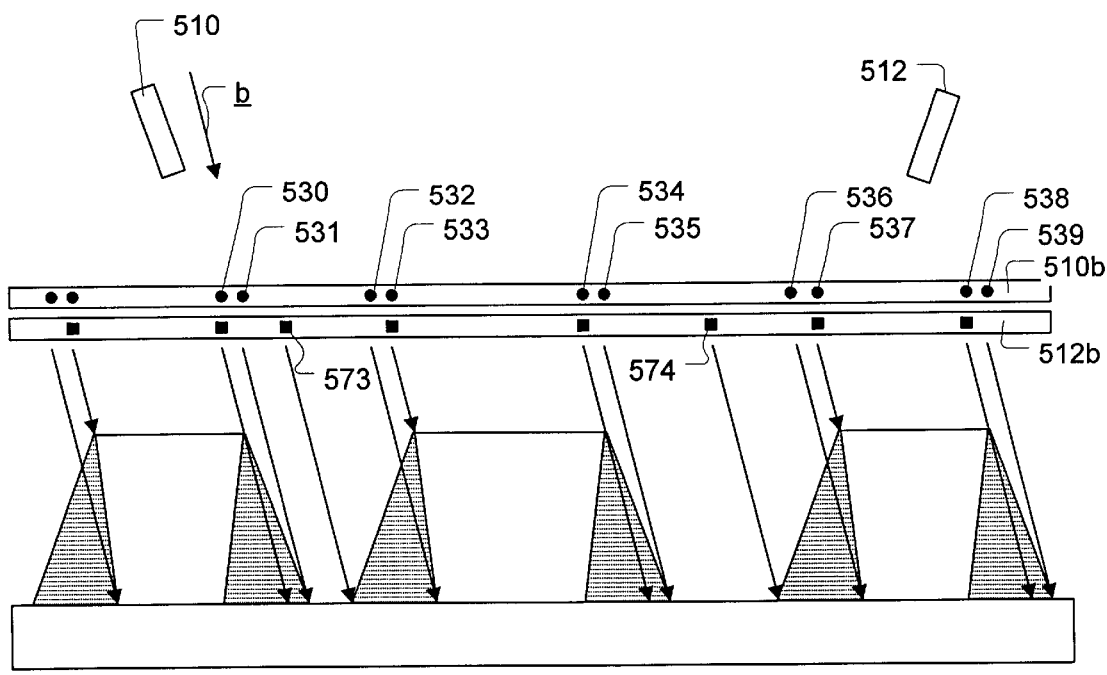
FIG. 5b is a cross-sectional illustration of a substrate showing critical positions of another of the beams employed in a scan and the transition points in secondary electron data resulting from the interaction of that beam with the substrate.

FIGS. 5a–5d illustrate a particular example in which a substrate 500 having raised lines 502 with reentrant profiles is scanned using a system providing two electron beams, a and b, and two secondary electron detectors, 510 and 512. FIGS. 5a and 5b are schematic illustrations showing beam positions where transitions occur in secondary electron intensity. The shaded areas to either side of the raised lines 502 mark areas shaded from the view of one or the other secondary electron detector. The arrows in FIG. 5a mark positions for beam a at which there occur transitions in secondary electron intensity at one or the other secondary electron detector. The open circles 520–527 within boxed area 510a mark locations of electron beam a at which transitions are observed by secondary electron detector 510 as a result of interaction of substrate 500 with electron beam a. The filled circles 530–539 in the boxed area 510b mark locations of electron beam b at which transitions are observed by secondary electron detector 510 as a result of interaction of substrate 500 with electron beam b. These transitions, and the opened and closed circles that mark their locations, may be referred to as signals. Signals received by secondary electron detector 512 are marked by the open and filled squares in boxed areas 512a and 512b.

Signals resulting from interactions of substrate 500 with electron beams a and b are superimposed in the output of each secondary electron detector, as illustrated by FIG. 5c. Nonetheless, signals from the two beams may be distinguished from one another in various ways and the data used to calculate critical dimensions, such as the upper widths of the features 502, the lower widths of the features 502, and the heights of features 502, and to form an image of the surface.

For example, the upper widths of features 502 may be determined from the spacing between transitions that are caused by one beam crossing the upper edges 540–545. The analysis involves distinguishing those transitions caused by beams crossing upper edges 540–545 from transitions caused by beams crossing lower corner 550–551 and those caused by beams crossing shadow edges 560–565. The analysis also involves distinguishing transitions caused by the interaction of substrate 500 with electron beam a from those caused by interactions with electron beam b.

Transition signals caused by electron beams crossing upper edges 540–545, such as those resulting in transition signals 520, 521, 523, 524, 526, 527, 530, 533, 534, 537, and 538 from secondary electron detector 510, can be distinguished from other transition signals by the fact that only transition signals caused by electron beams crossing upper edges 540–545 are detected by both secondary electron detectors simultaneously. This is illustrated in FIG. 5c, where for each of the transition signals 520, 521, 523, 524, 526, 527, 530, 533, 534, 537, and 538, represented by circles in boxed area 510ab, there is a corresponding signal from secondary electron detector 512 represented by a square in boxed area 512ab.

Transition signals caused by electron beams crossing upper edges 540–545 can also be distinguished from other transition signals based on differences in shape of the transitions. For example, the transitions caused by the electron beams passing in and out of shadows are smooth, whereas those caused by electron beams crossing upper edges 540–545 are jagged due to the special effects that occur when an electron beam crosses a corner. The shapes of transition caused by beams crossing lower corners also have distinctive shapes and can likewise be distinguished from transitions caused by beams crossing upper edges 540–545. The magnitudes of changes in secondary electron intensity across transitions provides further indications of transition type.

Transition signals resulting from one beam's interaction with the substrate may also be distinguished from transition signals resulting from the other beam's interaction with the substrate. For example, the magnitudes of changes in secondary electron intensities across transitions are different for the two beams and may be used to distinguish transition signals caused by one electron beam from those caused by the other.

Referring to FIGS. 5a and 5b, assuming the scans of beams a and b are from left to right, when electron beam a crosses leading edges of feature 502, at upper corners 540, 542, and 544 for example, the changes in secondary electron intensity are relatively small because the transitions are from beam a striking the surface of substrate 500 to beam a striking an upper surface of a feature 502. These surfaces all have approximately the same orientation. When beam b crosses these leading edges, however, the transitions are from beam b striking a side surfaces of a feature 502 to beam b striking a top surfaces of a features 502. These surfaces have different orientations. Therefore, the changes in intensity that occur when beam b crosses leading edges 540, 542, and 544 are larger and of different shape than the changes in intensity that occur when beam a crosses these leading edges. Thus, transition signals from beam a crossing a leading edge may be distinguished from transition signals from beam b crossing a leading edge. Extending the analysis, it may be determine for each upper corner transition signal whether it is associated with a leading or a trailing edge of a features 502 and whether the transition signal is associated with beam a or beam b.

Another method of distinguishing upper corner transition signals resulting from beam a from those resulting from beam b relies on the fact that the aggregate transition signals contains two repetitions of a single pattern. In the present example, where the upper surfaces of features 502 are all at the same height, the second repetition is at an approximately fixed offset dx from the first, as illustrated in FIG. 5c. For example, signals 523 and 524 are the substrate distance apart as signals 533 and 534, and thus the offset between signals 523 and 533 must be approximately the same as the offset between signals 524 and 534. Once the correct offsets are identified, the signals match up and can be separated into a set corresponding to beam a and a set corresponding to beam b. Once the upper corner transition signals associated with beam a are distinguished from those associated with beam b, either those of beam a or those of beam b may be used to calculate the upper widths of feature 502.

Feature heights may be determined from the locations of shadow transition signals, which are the transition signals that result from beams passing in and out of shadows. As noted previously, these transition signals can be distinguished from other types based on their smoothness. They may also be distinguished from lower corner transition signals based on the fact that shadow transition signals form a repeated pattern. As illustrated in FIG. 5d, the repeated pattern has fixed offsets, dy, where the surfaces of substrate 500 between features 502 all have the same height.

The heights of features 502 may be calculated from differences between dx and dy, or alternatively from distances between shadow transition signals and upper corner transition signals.

The lower widths of features 502 are determined from the locations of lower corner transitions. Lower corner transitions are all those that are neither shadow transitions nor upper corner edge transitions. Secondary electron detector 510 detects lower corner transitions associated with left hand side lower corners and secondary electron detector 512 detects lower transitions associated with right hand side lower corners. Left and right hand side lower corner transitions may be related to one another and used to calculate lower feature dimension using the offsets dy determined from the shadow transitions. Alternatively, lower feature widths may be determined from distances between lower corner transitions and adjacent upper corner transitions together with knowledge of the feature heights, as previously described.

One of ordinary skill in the art will recognize from the foregoing discussion that there are a plethora of ways in which secondary electron data that results from the interaction of multiple electron beams with a substrate may be analyzed. The methodology selected will depend on the SEM system, the substrate being analyzed, and the substrate feature characteristics of interest. Repeated patterns, feature of uniform height, and surfaces of uniform orientation all simplify the data analysis, but the redundancy in the forgoing analysis indicates that the substrate features may be considerably less regular than those in the foregoing example, which was selected for descriptive purposes.

Analysis of secondary electron data may be simplified and made more reliable by coordinating the scans of the two electron beams so that the locations where the beams strike the substrate remain proximate to one another. Coordinating the scans of two electron beams simplifies pattern matching operations, as only a small group of signals need be searched for matches. The probability of transition signals overlapping can be reduced in a coordinated scan by an appropriate choice of beam spacing in relation to substrate feature dimensions. When overlapping does occur, or there is an ambiguity in the data having some other cause, a small portion of a scan can be easily repeated, for example, with a different beam spacing or only one beam. All scan data within a small area may be obtained within a short time interval, facilitating real time, and near real time, imaging.

The two beams are considered proximate to one another if there are no more than about 10 transitions, from the point of view of a secondary electron detector, between a given transition caused by one beam's crossing a location on the substrate and the other beam crossing that same location. In one aspect of the invention, there are no more than about 2 transitions that take place between one beam's crossing any given location and the other beam crossing that same location. In another aspect of the invention, two beams strike individual features on the substrate surface simultaneously. The beams may be directed to overlap. For example, they may be directed to overlap when crossing upper corners of raised features or when crossing in and out of shadowed regions. The system may include feedback control to adjust the direction of one or more beams to maintain or re-establish proximity of the beams, or beam overlap, during the course of a scan, as may be desirable, for example, when raised surface features have gradually varying height causing unadjusted beams to gradually diverge.

What has been described above is the present invention and several of its specific aspects. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A scanning electron microscope, comprising:
   an electron beam source;
   electromagnetic elements configured to simultaneously direct with substantially differing angles of incidence a first and second electron beam against a substrate; and
   a first secondary electron detector configured to detect at least secondary electrons resulting from an interaction of the substrate with the first electron beam.

2. The scanning electron microscope of claim 1, wherein the angles of incidence of the first and second electron beams differ by at least about 10 degrees.

3. The scanning electron microscope of claim 2, wherein the angles of incidence of the first and second electron beams differ by at least about 20 degrees.

4. The scanning electron microscope of claim 1, wherein the first and second electron beams are configured to strike the substrate at first and second positions, the first and second positions being spaced apart by at least about one micron.

5. The scanning electron microscope of claim 4, wherein the first and second positions are spaced apart by at least about 100 microns.

6. The scanning electron microscope of claim 1, further comprising a second secondary electron detector.

7. The scanning electron microscope of claim 6, wherein:
   the angle of incidence of the first electron beam is tilted at least about 5 degrees from an imaginary plane;
   the angle of incidence of the second electron beam is tilted at least about 5 degrees from the imaginary plane in a different direction from the imaginary plane than that in which the first electron beam is tilted;
   the angle of an imaginary line from the first secondary electron detector to a point about where the first electron beam strikes the substrate is tilted at least about 5 degrees from the imaginary plane in the same direction from the imaginary plane as that in which the first electron beam is tilted; and
   the angle of an imaginary line from the second secondary electron detector to a point about where the second electron beam strikes the substrate is tilted at least about 5 degrees from the imaginary plane in the same direction from the imaginary plane as that in which the second electron beam is tilted.

8. The scanning electron microscope of claim 7, wherein:
   the angle of the imaginary line from the first secondary electron detector is tilted at least about 2 degrees further from the imaginary plane than the first electron beam; and
   the angle of the imaginary line from the second secondary electron detector is tilted at least about 2 degrees further from the imaginary plane than the second electron beam.

9. The scanning electron microscope of claim 6, wherein:
   the first secondary electron detector essentially detects only secondary electrons resulting from the interaction of the substrate with the first electron beam; and
   the second secondary electron detector essentially detects only secondary electrons resulting from an interaction of the substrate with the second electron beam.

10. The scanning electron microscope of claim 9, further comprising a plate that prevents secondary electrons resulting from the interaction of the substrate with the second electron beam from reaching the first secondary electron detector.

11. The scanning electron microscope of claim 9, further comprising electromagnetic element that prevent secondary electrons resulting from the interaction of the substrate with the second electron beam from reaching the first secondary electron detector.

12. A system for measuring a characteristic of a reentrant topographical feature of a substrate, comprising:
    means for simultaneously directing two or more electron beams at the substrate surface wherein two of the beams are directed at angles differing by at least about 10 degrees; and
    means for detecting secondary electrons produced by the interaction of the substrate with the electron beams.

13. The system of claim 12, wherein two of the beams are directed at angles differing by at least about 20 degrees.

14. A method for assessing a characteristic of a feature of a substrate surface, the method comprising:
    scanning the substrate simultaneously employing first and second electron beams directed against the substrate, the first and second electron beams having angles of incidence that differ by at least about 10 degrees;
    detecting secondary electrons produced by an interaction of the first and second electron beams with the substrate to generate secondary electron data; and
    analyzing the secondary electron data to assess the characteristic of the feature of the substrate surface.

15. The method of claim 14, wherein the angles of incidence of the two beams differ by at least about 20 degrees.

16. The method of claim 14, wherein secondary electrons produced by the interaction of the first electron beam with the substrate are detected separately from secondary electrons produced by an interaction of the second electron beam with the substrate.

17. The method of claim 14, further comprising rotating the substrate.

18. The method of claim 14, wherein the feature of the substrate is a raised line or trench with a reentrant profile and the characteristic assessed relates to the reentrant profile.

19. A scanning electron microscope system, comprising:
an electron beam source;
electromagnetic elements for simultaneously directing first and second electron beams with substantially differing angles of incidence derived from the electron beam source against a substrate;
a first secondary electron detector for simultaneously detecting secondary electrons resulting from the interaction of the substrate with the first electron beam and secondary electrons resulting from the interaction of the substrate with the second electron beam and for sending data relating to the secondary electrons detected; and
a processor for receiving and analyzing the data from the secondary electron detector.

20. The scanning electron microscope system of claim 19, wherein the system employs a portion of the data to determine where to direct the second electron beam.

21. The scanning electron microscope system of claim 19, further comprising a second secondary electron detector for detecting secondary electrons produced by the interaction of the substrate with the first and second electron beams and for sending data relating to the secondary electrons detected.

22. The scanning electron microscope system of claim 21, wherein the processor is configured to employ data from one of the secondary electron detectors in analyzing data from the other secondary electron detector.

23. The scanning electron microscope system of claim 19, wherein the processor is configured to detect a repeated pattern within the data.

24. The scanning electron microscope system of claim 19, wherein the processor is configured to distinguish different types of transition signals that occur within the data.

25. The scanning electron microscope system of claim 24, wherein the processor is configured to distinguish transition signals resulting from shadow transitions from other types of transitions.

26. The scanning electron microscope system of claim 24, wherein the processor is configured to distinguish transition signals resulting from the interaction of the substrate with one electron beam from transition signals resulting from the interaction of the substrate with the other electron beam.

27. The scanning electron microscope system of claim 19, wherein the electromagnetic elements give the first and second electron beams angles of incidence differing by at least about 10 degrees.

28. The scanning electron microscope system of claim 27, wherein the system is configure to synchronize scanning of the first and second electron beams, whereby the beams strike the substrate in proximity to one another.

29. The scanning electron microscope system of claim 28, wherein the first and second electron beams overlap in striking the substrate.

30. The scanning electron microscope system of claim 27, wherein the system is configure to synchronize scanning of the first and second electron beams, whereby the beams strike individual features on the surface of the substrate simultaneously.

31. A system for measuring a characteristic of a reentrant topographical feature of a substrate, comprising:
means for simultaneously directing two or more electron beams at the substrate, the beams having angles differing by at least about 10 degrees;
means for detecting secondary electrons resulting from the interaction of the substrate with the electron beams and producing secondary electron data; and
means for analyzing the secondary electron data;
wherein the secondary electrons resulting from the interaction of the substrate with two or more of the electron beams are detected together.

32. A method for assessing a characteristic of a feature of a substrate surface, the method comprising:
scanning the substrate simultaneously employing first and second electron beams with substantially differing angles of incidence directed against the substrate;
detecting secondary electrons resulting from an interaction of the first electron beam with the substrate together with secondary electrons resulting from an interaction of the second electron beam with the substrate to generate secondary electron data; and
analyzing the secondary electron data to assess the characteristic of the feature of the substrate surface.

33. The method of claim 32, wherein the first and second electron beams have angles of incidence with respect to the substrate that differ by at least about 10 degrees.

34. The method of claim 32, wherein the angles of incidence differ by at least about 20 degrees.

35. The method of claim 33, wherein analyzing the secondary electron data comprises locating a repeated pattern within the data.

36. The method of claim 35, wherein the repeated pattern is a pattern occurring within the data from a single secondary electron detector.

37. The method of claim 33, wherein analyzing the secondary data comprises analyzing data from a second secondary electron detector.

38. The method of claim 37, wherein analyzing the secondary electron data comprises locating a pattern repeated between the secondary electron data from the first secondary electron detector and the secondary electron data from the second secondary electron detector.

39. The method of claim 33, wherein analyzing the secondary electron data comprises distinguishing different types of transition signals that occur within the data.

40. The method of claim 39, wherein analyzing the secondary electron data comprises distinguishing transition signals resulting from shadow transitions from transition signals resulting from other types of transitions.

41. The method of claim 39, wherein analyzing the secondary electron data comprises distinguishing transition signals resulting from the interaction of the substrate with one electron beam from transition signals resulting from the interaction of the substrate with the other electron beam.

* * * * *